(12) United States Patent
Schattenmann et al.

(10) Patent No.: US 6,288,257 B1
(45) Date of Patent: Sep. 11, 2001

(54) METHOD FOR MAKING TETRAORGANOOXYSILANES

(75) Inventors: Florian Johannes Schattenmann, Ballston Lake; Larry Neil Lewis, Scotia, both of NY (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 09/378,642

(22) Filed: Aug. 20, 1999

(51) Int. Cl.$^7$ ..................................................... C07F 7/04
(52) U.S. Cl. ............................. 556/470; 556/483; 423/325
(58) Field of Search ..................................... 556/483, 325, 556/470

(56) References Cited

U.S. PATENT DOCUMENTS 2,473,260   6/1949   Rochow ............................ 260/448.8
5,583,085 * 12/1996  Ward ................................. 502/232

OTHER PUBLICATIONS

Ono et al., "Direct Synthesis of Tetraalkoxysilanes from Silica by Reaction with Dialkyl Carbonates", Chemical Materials, vol. 5, pp 442–447, 1993.*

"Direct Synthesis of Tetraalkoxysilanes from Silica by Reaction with Dialkyl Carbonates", Y. Ono, M. Akiyama and E. Suzuki, Chem. Mater. 1993, 5, 442–447.

"Short Communication", M. Akiyama, E. Suzuki and Y. Ono, Inorganica Chimica Acta, 207 (1993) 259–261, 259–261.

"Synthesis of Pentacoordinate Silicon Complexes from SiO2", R. Laine, K. Blohowiak, T. Robinson, M. Hoppe, P. Nardi, J. Kampf & J. Uhm, Nature—vol. 353, Oct. 17, 1991—642–644.

"Direct Synthesis of Alkoxysilanes by Gas–solid Reactions", E. Suzuki, M. Okamoto, & Y. Ono, Sekiyu Gakkaishi, vol. 37, No. 2, 1994, 103–111.

Rosenheim et al. (Z. Anorg. Allg. Chem. 1931 –196, 160 "Inner Complex Pyrocatecholates of Tetravalent Elements", pp. 1–17 and English Translation).

* cited by examiner

Primary Examiner—Margaret G. Moore
(74) Attorney, Agent, or Firm—Bernadette M. Bennett; Noreen C. Johnson

(57) ABSTRACT

A method for the preparation of tetraorganooxysilanes is provided which comprises reaction of a natural silicon dioxide source with an organo carbonate.

20 Claims, No Drawings

METHOD FOR MAKING TETRAORGANOOXYSILANES

STATEMENT REGARDING FEDERALLY SPONSORED RESEARCH & DEVELOPMENT

The government may have certain rights in this intention pursuant to contract number DE-FC02-98CH 10931 awarded by the United States Department of Energy.

BACKGROUND OF THE INVENTION

The present invention relates to a method for making tetraorganooxysilanes. More particularly, the present invention relates to a process involving the reaction of a natural silicon dioxide source in the presence of an organo carbonate.

Tetraorganooxysilanes are silicon-containing compounds of the formula $(RO)_4Si$ where R is an alkyl group, aryl group or mixture thereof. Tetraorganooxysilanes include tetraalkoxysilanes, tetraaryloxysilanes, and mixed tetra (alkoxyaryloxy)silanes. Silicon-containing compounds, such as tetraorganooxysilanes, are commonly made using manufactured silicon dioxide as a starting material. Unfortunately, manufactured silicon dioxide is not an energy efficient source of silicon. Hence, different sources of silicon to synthesize silicon-containing compounds are constantly being examined.

The process commonly used commercially for the production of silicones and more particularly, alkoxysilanes, was first described by Rochow et al., U.S. Pat. No. 2,473,260. The Rochow process uses silicon, also referred to as elemental silicon, as a starting material. The elemental silicon must first be reduced from silicon dioxide. The elemental silicon is then oxidized to yield alkoxysilanes via a reaction of the silicon with methanol in the presence of a copper catalyst. It is well known in the art that the silicon-oxygen bond in silicon dioxide is extremely stable. In order to break the silicon-oxygen bond, a large amount of energy is consumed when silicon dioxide is reduced to elemental silicon. Thus, due to the large amount of energy needed to break the silicon-oxygen bond, the synthesis of silicones from silicon dioxide and the Rochow process is expensive and not energy efficient.

In other work related to the invention, several complex compounds have been studied for the synthesis of silicon-containing compounds. Rosenheim et al. (*Z. Anorg. Allg. Chem.* 1931, 196, 160) described the formation of hexacoordinated dianionic complexes from silica under basic conditions. Silica, sand and quartz powder were depolymerized in the presence of alkali catecholates.

Other methods for the synthesis of silicon-containing compounds have been described which do not use silicon dioxide as a starting material. Laine et al. (*Nature* 1991, 353, 642) published a method for synthesizing pentatcoordinate silicates from silica, ethylene glycol, and base. The pentacoordinate silicate produced is a highly reactive compound which can be a useful precursor of new silicone compounds.

Ono, Akiyama and Suzuki (*Chem. Mater.* 1993, 5, 442) reported that silica gel reacts with gaseous dimethyl carbonate (DMC) at 500° K. to 600° K. to yield tetramethoxysilane in the presence of a catalyst supported on the silica. Ono et al. (*Inorg. Chim. Acta* 1993, 207, 259) also determined that rice hull ash, which has 92% silicon dioxide purity, also reacts with dimethyl carbonate in the presence of a catalyst at 625° K. However, silica gel as well as rice hull ash are manufactured materials and do not provide significant cost advantage over the well-established route to tetraalkoxysilanes through elemental silicon.

In the past, the synthesis of silicon-containing compounds has relied heavily on the reduction of silicon dioxide to elemental silicon. Unfortunately, the large amount of energy needed for synthesizing silicones such as tetraorganooxysilanes from silicon dioxide can be problematic. Thus, new synthetic routes are constantly being sought which rely on an efficient energy source of silicon dioxide.

BRIEF SUMMARY OF THE INVENTION

The present invention provides a method for the preparation of tetraorganooxysilanes comprising reaction of a natural silicon dioxide source with an organo carbonate.

DETAILED DESCRIPTION OF THE INVENTION

The present invention relates to a process involving the reaction of a natural silicon dioxide source with an organo carbonate. Organo carbonates are of the general formula, $R_2CO_3$ where R is an alkyl group, aryl group or mixture thereof. Natural silicon dioxide sources have been found to be energy efficient and cost effective starting materials for the formation of tetraorganooxysilanes. Silicon dioxide comprises one atom of silicon and two atoms of oxygen. "Source" as used herein refers to the material which provides the silicon necessary to synthesize tetraorganooxysilanes. "Natural silicon dioxide" as used herein refers to naturally occurring silicon dioxide which is found in non-living matter in the earth. Natural silicon dioxide is typically mined and dried. Natural silicon dioxide can also be calcined or flux calcined. Natural silicon dioxide sources are well known in the art and are illustrated by minerals and diatomaceous earth. Typical minerals include, for example, neosilicates, sorosilicates, cyclosilicates, inosilicates, phyllosilicates, and tectosilicates.

Tetraorganooxysilanes are of the formula $(RO)_4Si$ where R is an alkyl group, aryl group, or mixture thereof. Typical tetraorganooxysilane products include tetraalkoxysilanes such as tetramethoxysilane, tetraethoxysilane, and tetraisopropoxysilane; tetraaryloxysilanes such as tetraphenoxysilane; as well as mixed tetra(alkoxyaryloxy)silanes such as dimethoxydiphenoxysilane.

Diatomaceous earth is a common source for natural silicon dioxide. Diatomaceous earth (DE) refers to sedimentary rocks that are mainly composed of fossilized single-celled diatoms. Diatoms are minute organisms which are abundant in both freshwater and seawater. These organisms fossilize to form diatomaceous earth. Diatomaceous earth is generally composed of amorphous silicon dioxide. "Amorphous" as used herein reters to a mineral or diatomaceous earth that does not have a definite crystalline structure.

The method for synthesizing tetraorganooxysilanes and in particular, tetramethoxysilane $[Si(OMe)_4]$, begins with the treatment of the diatomaceous earth. The diatomaceous earth provides the silicon backbone for the tetraorganooxysilane. Initially, the diatomaceous earth is combined with a catalyst by stirring in an aqueous solution. Useful catalysts comprise at least one alkali metal hydroxide and alternatively, at least one alkali metal halide and combinations thereof. Examples of alkali metal hydroxides and alkali metal halides include, but are not limited to, sodium hydroxide, potassium hydroxide, rubidium hydroxide, cesium hydroxide, cesium fluoride, potassium fluoride, potassium chloride, sodium chloride and combinations thereof. The step of stirring the diatomaceous earth in the aqueous solution with the catalyst typically breaks up the diatomaceous earth to force a suspension. "Suspension" as used herein refers to undissolved solid particulates mixed in a liquid. At least portions of the catalyst chemically binds to the silicon dioxide. After the diatomaceous earth and catalyst are mixed in an aqueous solution, the material is then heated to dryness and ground into a powder of diatomaceous earth-catalyst complex. "Dryness" as used herein refers to a water content of less than about 1% by weight.

The next step in the method of the present invention is the reaction of the diatomaceous earth-catalyst complex with an organo carbonate. The reaction commonly can be practiced in a fixed bed reactor. The method for preparation of tetraorganooxysilanes, however, can be performed in other types of reactors, such as fluid bed reactors and stirred bed reactors. More specifically, the fixed bed reactor is a column that contains diatomaceous earth-catalyst complex wherein a carrier gas, such as an inert gas, is passed through. Organo carbonate is fed into the carrier gas stream. A stirred bed is similar to a fixed bed in which there is mechanical agitation of some sort in order to keep the bed in constant motion. A fluidized bed reactor, on the other hand, is a bed comprising diatomaceous earth-catalyst complex which is fluidized; that is the diatomaceous earth complex is suspended in the gas, typically argon, that is passed through the reactor. Reaction typically occurs at a temperature in a range between about 280° C. and about 360° C. and commonly, in a range between about 320° C. and about 350° C.

The reaction of the present invention can be performed in batch, continuous, or semi-continuous mode. With a batch mode reaction, for instance, all of the solid components are combined and reacted until most of the solids are consumed. In order to proceed, the reaction has to be stopped and additional solid added. A fixed bed and stirred bed may both be run under batch conditions. In contrast, a fluidized reactor is typically run under continuous conditions. With continuous conditions, the reaction does not have to be stopped in order to add more solid reactants.

Suitable organo carbonates typically comprise at least one dialkyl carbonate, diaryl carbonate, or alkyl aryl carbonate. A typical organo carbonate is dimethyl carbonate. Other organo carbonates useful for the present invention comprise diphenyl carbonate, ethylene carbonate and similar compounds.

The organo carbonate is typically added to the reactor via any convenient method to provide batch, continuous, or semi-continuous means of addition. A pumping device, such as a motor driven syringe, is an example of a continuous means of addition. A motor driven syringe allows for consistent amounts of organo carbonate to be added to the reaction mixture at given time intervals. Addition of the organo carbonate via a motor driven syringe is illustrative and non-limiting. Manual injection is also a common method for the addition of organo carbonates. The organo carbonate is typically added in a mole ratio of organo carbonate to silicon dioxide in a range between about 1:1 and about 15:1 and commonly, a mole ratio of organo carbonate to silicon dioxide in a range between about 8:1 and 12:1.

Products in the tetraorganooxysilane synthesis may be isolated by any convenient means. Typically, product(s) may be isolated by distillation into fractions typically referred to as condensate. Once the fractions are collected, the formation of the tetraorganooxysilane may be confirmed by such methods as gas chromatography-mass spectroscopy and proton nuclear magnetic resonance spectroscopy.

An important advantage of using a natural silicon dioxide source such as diatomaceous earth or minerals as starting materials for the preparation of tetraorganooxysilanes is that it is energy efficient. The present invention does not require the reduction of silicon dioxide to elemental silicon. Thus, the energy advantage of the present invention is a significant advancement over prior art syntheses. The invention also encompasses using silicon dioxide sources that include some minor percentage by weight of synthetic, particularly, recycled silicon dioxide.

Tetraorganooxysilanes obtained by the present me,-hod may be used in a wide variety of applications. For example, tetraorganooxysilanes may be used as coupling agents, precursors to pure and ultra-pure silicon dioxide, additives for plastic applications, and adhesion promoters.

In order that those skilled in the art will be better able to practice the invention, the following examples are given by way of illustration and not by way of limitation.

EXAMPLE 1

This example illustrates the preparation of tetramethoxysilane using flux calcined diatomaceous earth, CELITE SNOW FLOSS. CELITE SNOW FLOSS (0.82 grams) was stirred in an aqueous solution of 4.5 weight % potassium hydroxide to form a suspension. The suspension was heated to dryness and the solid obtained was further dried overnight at 115° C. The material was ground and charged in a fixed bed flow reactor in a vertical furnace. The solid was kept at a reaction temperature of 320° C. for 1 hour. Dimethyl carbonate in a total amount in a range between about 8 milliliters and about 10 milliliters was fed using a motor driven syringe at 1.6 milliliters/hour into an argon carrier gas stream flowing it 20 milliliters gas per minute. The condensate products were collected in fractions using a water chilled condenser. Results in percent by weight tetramethoxysilane based on total condensate produced are set forth in Table 1. Mass in grams is the mass of the condensate.

TABLE 1

| Fraction | Mass (grams) | % Si(OMe)$_4$ |
| --- | --- | --- |
| 1 | 0.41 | 3.47 |
| 2 | 0.79 | 10.02 |
| 3 | 0.51 | 11.54 |
| 4 | 0.47 | 11.89 |
| 5 | 0.66 | 9.44 |
| 6 | 0.71 | 6.70 |
| 7 | 0.75 | 5.68 |
| 8 | 0.35 | 4.41 |

EXAMPLE 2

The synthesis of tetramethoxysilane was identical to Example 1 with variance in the reaction temperature. The CELITE SNOW FLOSS was present at 0.82 grams. The aqueous solution used contained 4.5% by weight potassium hydroxide. The addition of dimethyl carbonate occurred in a fixed bed reactor at a reaction temperature of 350° C. The results in percent by weight tetramethoxysilane based on total condensate produced are set forth in Table 2. Mass in grams is the mass of condensate.

TABLE 2

| Fraction | Mass (grams) | % Si(OMe)$_4$ |
|---|---|---|
| 1 | 0.43 | 6.78 |
| 2 | 0.37 | 14.01 |
| 3 | 0.35 | 17.45 |
| 4 | 0.40 | 16.42 |
| 5 | 0.39 | 10.90 |
| 6 | 0.14 | 10.97 |

EXAMPLE 3

Tetramethoxysilane was prepared under identical conditions to Example 1 with a variance in the amount of diatomaceous earth used. CELITE SNOW FLOSS was present at 0.20 grams. Potassium hydroxide (4.5% by weight) was present in the aqueous solution. The addition of dimethyl carbonate occurred in a fixed bed reactor at a reaction temperature of 320° C. The results in percent by weight tetramethoxysilane based on total condensate produced are set forth in Table 3. Mass in grams is the mass of the condensate.

TABLE 3

| Fraction | Mass (grams) | % Si(OMe)$_4$ |
|---|---|---|
| 1 | 0.36 | 0.31 |
| 2 | 0.58 | 2.49 |
| 3 | 0.54 | 3.04 |
| 4 | 1.25 | 4.08 |
| 5 | 0.43 | 3.46 |
| 6 | 1.03 | 2.74 |
| 7 | 0.99 | 1.92 |
| 8 | 1.16 | 1.43 |

Analysis via gas chromatography-mass spectrometry and proton nuclear magnetic resonance spectroscopy revealed that the major component in the product stream was reacted dimethyl carbonate. Incomplete conversion of the dimethyl carbonate is acceptable since unreacted dimethyl carbonate can be recycled in the process for producing the tetraorganooxysilanes.

While typical embodiments have been set forth for the purpose of illustration, the foregoing description should not be deemed to be a limitation on the scope of the invention. Accordingly, various modifications, adaptations, and alternatives may occur to one skilled in the art without departing from the spirit and scope of the present invention.

What is claimed is:

1. A method for the preparation of tetraorganooxysilanes comprising reacting a "mineral silicon dioxide source, an amorphous silicon dioxide source or a mixture thereof" with an organo carbonate.

2. The method according to claim 1, wherein the tetraorganooxysilane comprises tetraalkoxysilanes, tetraaryoxysilanes or mixed tetra(alkoxyaryloxy)silanes.

3. The method according to claim 1, wherein the tetraorganooxysilane comprises tetramethoxysilane.

4. The method according to claim 1 wherein the organo carbonate comprises a dialkyl carbonate, diaryl carbonate, alkyl aryl carbonate or combinations thereof.

5. The method according to claim 1, wherein the organo carbonate comprises dimethyl carbonate.

6. The method according to claim 1, wherein the mineral silicon dioxide source is a mineral wherein the mineral comprises neosilicates, sorosilicates, cyclosilicates, inosilicates, phyllosilicates, tectosilicates or combinations thereof.

7. The method according to claim 1, where in the amorphous natural silicon dioxide source is diatomaceous earth.

8. The method according to claim 1, further comprising the step of treating the natural silicon dioxide source before reaction with the organo carbonate, the treatment comprising the steps of:

(I) combining the natural silicon dioxide source with a catalyst in aqueous solution to form a suspension; and (II) heating the suspension to dryness.

9. The method according to claim 8, wherein the catalyst comprises an alkali metal hydroxide, alkali metal halide, or combinations thereof.

10. The method according to claim 9, wherein the catalyst comprises sodium hydroxide, potassium hydroxide, rubidium hydroxide, cesium hydroxide, cesium fluoride, potassium fluoride, potassium chloride, sodium chloride, or combinations thereof.

11. The method according to claim 1, wherein the reaction occurs in a reactor bed which comprises a reactor selected from the group consisting of a fixed bed reactor, a fluidized bed reactor and a stirred bed reactor.

12. The method according to claim 11, wherein the reaction is operated in batch mode.

13. The method according to claim 11, wherein the reaction is operated in continuous mode.

14. The method according to claim 1, wherein the reaction is conducted at a temperature in the range between about 280° C. and about 360° C.

15. The method according to claim 14, wherein the reaction is conducted at a temperature in a range between about 320° C. and about 350° C.

16. The method according to claim 1, wherein the organo carbonate is present in a mole ratio of organo carbonate to silicon dioxide in a range between about 1:1 and about 15:1.

17. A method according to claim 16, wherein the organo carbonate is present in a mole ratio of organo carbonate to silicon dioxide in a range between about 8:1 and about 12:1.

18. A method for the preparation of tetramethoxysilane comprising the steps of:

(I) combining diatomaceous earth with potassium hydroxide in an aqueous solution to form a suspension;

(II) heating the suspension to dryness;

(III) reacting the silicon dioxide with an effective amount of dimethyl carbonate wherein the dimethyl carbonate is added in mole ratio of dimethyl carbonate to silicon dioxide in a range between about 8:1 and about 12:1;

(IV) recovering the synthesis products; and (V) recycling the organo carbonate.

19. The method according to claim 18, wherein the step of reacting the diatomaceous earth with dimethyl carbonate occurs in a fixed bed reactor at a temperature in a range between about 280° C. and about 350° C.

20. The method according to claim 19, wherein the step of reacting the diatomaceous earth with dimethyl carbonate occurs in a fixed bed reactor at a temperature in a range between about 320° C. and about 350° C.

* * * * *